(12) United States Patent
Robinson et al.

(10) Patent No.: US 7,081,244 B2
(45) Date of Patent: *Jul. 25, 2006

(54) NEISSERIAL VACCINE COMPOSITIONS AND METHODS

(75) Inventors: Andrew Robinson, Salisbury (GB); Andrew Richard Gorringe, Salisbury (GB); Michael John Hudson, Salisbury (GB); Philippa Bracegirdle, Salisbury (GB); John Simon Kroll, Oxford (GB); Paul Richard Langford, Oxford (GB); Steven Anthony Rochford Webb, Subiaco (AU); Keith Cartwright, Brobury (GB); Cliona Anne O'Dwyer, Furbo (IE)

(73) Assignees: Health Protection Agency, Salisbury (GB); Imperial College Innovations, Ltd., Salisbury (GB)

(*) Notice: Subject to any disclaimer, the term of this patent is extended or adjusted under 35 U.S.C. 154(b) by 0 days.

This patent is subject to a terminal disclaimer.

(21) Appl. No.: 10/185,769

(22) Filed: Jul. 1, 2002

(65) Prior Publication Data

US 2003/0021812 A1 Jan. 30, 2003

Related U.S. Application Data

(63) Continuation of application No. 09/914,041, filed as application No. PCT/GB00/00624 on Feb. 22, 2000, now abandoned.

(30) Foreign Application Priority Data

Feb. 22, 1999 (GB) .................................. 9904028.9
Sep. 23, 1999 (GB) .................................. 9922561.7

(51) Int. Cl.
*A61K 39/02* (2006.01)
*A61K 39/095* (2006.01)
*A61K 39/116* (2006.01)
*A61K 39/38* (2006.01)
*C07K 1/00* (2006.01)

(52) U.S. Cl. .............................. 424/234.1; 424/249.1; 424/250.1; 424/203.1; 424/200.1; 424/184.1; 514/2; 530/350; 530/825

(58) Field of Classification Search ............. 424/186.1, 424/200.1, 234.1, 235.1, 249.1, 203.1, 250.1; 514/2; 530/825, 350; 435/71.1, 69.3, 71.2, 435/69.1
See application file for complete search history.

(56) References Cited

U.S. PATENT DOCUMENTS

| 5,470,740 | A | 11/1995 | Longo et al. ............ 435/252.33 |
|---|---|---|---|
| 5,980,912 | A * | 11/1999 | Podolski et al. ........... 424/278.1 |
| 6,013,267 | A | 1/2000 | Blake et al. .............. 424/249.1 |
| 6,413,768 | B1 | 7/2002 | Galen ........................ 435/320.1 |
| 6,703,233 | B1 | 3/2004 | Galen ........................ 435/252.3 |
| 6,737,521 | B1 | 5/2004 | Fischetti et al. ............ 536/23.4 |
| 2003/0021812 | A1 | 1/2003 | Robinson et al. ......... 424/249.1 |
| 2003/0026809 | A1 | 2/2003 | Robinson et al. ......... 424/190.1 |
| 2003/0215469 | A1 | 11/2003 | Robinson et al. ......... 424/250.1 |

FOREIGN PATENT DOCUMENTS

| EP | 1 297 844 A2 | 4/2003 |
|---|---|---|
| WO | WO 96/29412 | 9/1996 |
| WO | WO 99/61620 A2 | 12/1999 |
| WO | WO 03/051379 A1 | 6/2003 |

OTHER PUBLICATIONS

Ferreiros et al. FEMS Microbiol. Lett. 83: 247-254, 1991.*
Russell et al. Can. J. Microbiol. 21: 1519-1534, 1975.*
Kim et al. Infect. immun. 57: 602-608, 1989.*
Hoen et al. Infect. immun. 58: 3929-3933, 1990.*
Cann, K. J. and Rogers, T.R., "Detection of antibodies to common antigens of pathogenic and commensal Neisseria species," *J. Med. Microbiol.* 30:23-30, The Pathological Society of Great Britain and Ireland (1989).
Gómez, J.A. et al., "Antigenicity, cross-reactivity and surface exposure of the *Neisseria meningitidis* 37 kDa protein (Fbp)," *Vaccine* 14:1340-1346, Elsevier Science Ltd (1996).
English abstract of Aoun, L. et al., "Human Antibody Response to the 70-KD Common Neisserial Antigen in Patients and Carriers of *Meningococci* or Non-Pathogenic *Neisseria*," *Annales de l'Institut Pasteur Microbiology* 139:203-212, Biosis Online accession No. PREV198886026860, XP-0021498186(1988).
Troncoso, G. et al., "Antigenic cross-reactivity between outer membrane proteins of *Neisseria meningitidis* and commensal *Neisseria* species," *FEMS Immunol. Med. Microbiol.* 27:103-109, Elsevier Science B.V. (Feb. 2000).

(Continued)

*Primary Examiner*—S. Devi
(74) *Attorney, Agent, or Firm*—Sterne, Kessler, Goldstein & Fox P.L.L.C.

(57) ABSTRACT

Methods and compositions for the treatment of microbial infection, and in particular meningococcal disease, comprise a commensal *Neisseria* or an extract of a commensal *Neisseria*. Further methods and compositions comprise conimensal *Neisseria* which express genes from virulent strains of *Neisseria* and/or heterologous gene products from non-Neisserial sources. Such compositions are used in vaccine preparations for the treatment of microbial infection.

11 Claims, 5 Drawing Sheets

OTHER PUBLICATIONS

Ala'Aldeen, D.A.A., "Transferrin receptors of *Neisseria meningitidis*: promising candidates for a broadly cross-protective vaccine," *J. Med. Microbiol. 44*:237-243, Lippincott, Williams & Wilkins (1996).

Evans, T.M., "Molecular Cloning and Characterization of an Oxygen-Regulated Gonococcal Outer Membrane Protein," *Dissertation Abstracts International 50*:3315, The University of Rochester (1989).

Fusco, P.C., et al., "Meningococcal vaccine development: a novel approach," *Exp. Opin. Invest. Drugs 7*:245-252, Ashley Publications Ltd. (Feb. 1998).

Gómez, J.A., et al., "Effect of adjuvants in the isotypes and bactericidal activity of antibodies against the transferrin-binding proteins of *Neisseria meningitidis*,"*Vaccine 16*:1633-1639, Elsevier Science Ltd. (Oct. 1998).

Grifantini, R., et al., "Gene Expression Profile in *Neisseria meningitidis* and *Neisseria lactamica* upon Host-Cell Contact," *Ann. N.Y. Acad. Sci. 975*:202-216, New York Academy of Sciences (Dec. 2002).

Linz, B., et al., "Frequent interspecific genetic exchange between commensal neisseriae and *Neisserle meningitidis*," *Molec. Microbiol. 36*:1049-1058, Blackwell Science Ltd. (Jun. 2000).

Martin, D., et al., "Highly Conserved *Neisseria meningitidis* Surface Protein Confers Protection against Experimental Infection," *J. Exp. Med. 185*:1173-1183, The Rockefeller University Press (1997).

Moe, G.R., et al., "Differences in Surface Expression of NspA among *Neisseria meningitidis* Group B Strains,"*Infection & Immunity 67*:5664-5675, American Society for Microbiology (November 1999).

Moe, G.R., et al., "Molecular mimetics of polysaccharide epitopes as vaccine candidates for prevention of *Neisseria meningitidis* serogroup B disease," *FEMS Immunol. Med. Microbiol. 26*:209-226, Elsevier Science B.V. (Dec. 1999).

Moe, G.R., et al., "Sequential Immunization with Vesicles Prepared from Heterologus *Neisseria meningitidis* Strains Elicits Broadly Protective Serum Antibodies to Group B Strains," *Infect. & Immun. 70*:6021-6031, American Society for Microbiology (Nov. 2002).

Oliver, K.J., et al., "*Neisseria lactamica* Protects against Experimental Meningococcal Infection," *Infect. & Immun. 70*:3621-3626, American Society for Microbiology (Jul. 2002).

Pannekoek, Y., et al., "Construction of recombinat neisserial Hsp60 proteins and mapping of antigenic domains," *Molec. Microbiol. 15*:277-285, Blackwell Science Ltd. (1995).

Parkhill, J., et al., "Complete DNA sequence of a serogroup A strain of *Neisseria meningitidis* Z2491," *Nature 404*:502-506, Macmillan Publishers Ltd. (Mar. 2000).

Pettit, R.K., et al., "Acid stress upregulated outer membrane proteins in clinical isolates of *Neisseria gonorrhoeae*, but not most commensal Neisseria," *Can. J. Microbiol. 47*:871-876, National Research Council of Canada (Sep. 2001).

Zhou, J., et al., "Interspecies recombination, and phylogenetic distortions, within the glutamine synthetase and shikimate dehydrogenase genes of *Neisseria meningitidis* and commensal *Neisseria species*," *Molec. Microbiol. 23*:799-812, Blackwell Science Ltd. (1997).

Copy of Office Action for U.S. Appl. No. 09/942,583, Robinson et al., filed Aug. 31, 2001, mailed May 8, 2003.

Copy of Office Action for U.S. Appl. No. 09/942,583, Robinson et al., filed Aug. 31, 2001, mailed Jan. 5, 2004.

Copy of Office Action for U.S. Appl. No. 09/942,583, Robinson et al., filed Aug. 31, 2001, mailed Jul. 28, 2004.

Aho, E.L., et al., "A comparative analysis of pilin genes from pathogenic and nonpathogenic *Neisseria* species," *Microbial Pathogenesis 28*:81-88, Academic Press (Feb. 2000).

Aho, E.L., et al., "Characterization of a Class II Pilin Expression Locus from *Neisseria meningitidis*: Evidence for Increased Diversity among Pilin Genes in Pathogenic *Neisseria* Species," *Infection and Immunity 65*:2613-2620, American Society for Microbiology (1997).

Bennett, J.S., et al., "Genetic Diversity and Carriage Dynamics of *Neisseria lactamica* in Infants," *Infection and Immunity 73*:2424-2432, American Society for Microbiology (Apr. 2005).

Claassen, I., et al., "Production, characterization and control of a *Neisseria meningitidis* hexavalent class 1 outer membrane protein containing vesicle vaccine," *Vaccine 14*:1001-1008, Elsevier Science Ltd. (1996).

Ellis, R.W., "New technologies for making vaccines," *Vaccine 17*:1596-1604, Elsevier Science Ltd. (1999).

Goh, L.L., et al., "Molecular cloning and functional characterization of fumarase C in *Neisseria* species," *Antoine van Leeuwenhoek. 87*:205-213, Springer (Apr. 2005).

Gooringe, A., et al., "The development of a meningococcal disease vaccine based on *Neisseria lactamica* outer membrane vesicles," *Vaccine 23*:2210-2213, Elsevier Science Ltd. (Mar. 2005).

Gotschlich, E.C., et al., "Cloning of the Structural Genes of Three H8 Antigens and of Protein III of Neisseria Gonorrhoeae," *J. Exp. Med. 164*:868-881 (1986).

Humphries, H.E., et al., "Recombinant meningococcal PorA protein, expressed usinng a vector system with potential for human vaccination, induces a bactericidal immune response," *Vaccine 22*:1564-1569, Elsevier science Ltd. (Mar. 2004).

Jódar, L., et al., "Development of vacines against meningococcal disease," *Lancet 359*:1499-1508, The Lancet Publishing Group (Apr. 2002).

Johnson, S.R., et al., "Cloning and Characterization of the Catalase Gene of *Neisseria gonorrhoeae*: Use of the Gonococcus as a Host Organism for Recombinant DNA," *Infection and Immunity 64*:2627-2634, American Society for Microbiology (1996).

Locht, C., "Live bacterial vectors for intranasal delivery of protective antigens," *PSTT 3*:121-128, Elsevier Science (Apr. 2000).

Medaglini, D., et al., "Commensal bacteria as vectors for mucosal vaccines against sexually transmitted diseases: vaginal colonization with recombinant streptococci induces local and systemic antibodies in mice," *Vaccine 15*:1330-1337, Elsevier Science Ltd. (1997).

Mielcarek, N., et al., "Nasal vaccination using live bacterial vectors," *Advanced Drug Delivery Reviews 51*:55-69, Elsevier, B.V. (Sep. 2001).

Mukhopadhyay, T.K., et al., "Rapid characterization of outer-membrane proteins in *Neisseria lactamica* by SELDI-TOF-MS (surface-enhanced laser desorption ionization-time-of-flight MS) for use in a meningococcal vaccine," *Biotechnol. Appl. Biochem. 41*:175-182, Portland Press Ltd. (Apr. 2005).

O'Dwyer, C.A., et al., "Expression of Heterologous Antigens in Commensal *Neisseria* spp.: Preservation of Conformational Epitopes with Vaccine Potential," *Infection*

*and Immunity 72*:6511-6518, American Society for Microbiology (Nov. 2004).

Oftung, F., et al., "A mouse model utilising human transferrin to study protection against *Neisseria meningitidis* serogroup B induced by outer membrane vesicle vaccination," *FEMS Immunol. Med. Microbiol. 26*:75-82, Elsevier Science B.V. (1999).

Pollard, A.J. and Frasch, C., "Development of natural immunity to Neisseria *meningitidis,*" *Vaccine 19*:1327-1346, Elsevier Science Ltd. (Jan. 2001).

Sánchez, S, et al., "Evaluation of cross-reactive antigens as determinants of cross-bacterial activity in pathogenic and commensal Neisseria," Vaccine 19:3390-3398, Elsevier Science Ltd. (May 2001).

Serruto, D., et al., "Biotechnology and vaccines: applications of functional genomics to *Neisseria meningitidis* and other bacterial pathogens," *J. Biotechnol. 113*:15-32, Nature Publishing Group (Sep. 2004).

Tettelin, H., et al., "Complete Genome Sequence of *Neisseria meningitidis* Serogroup B Straiin MC58," *Science 287*:1809-1815, American Association for the Advancement of Science (Mar. 2000).

Toleman, M., et al., "Expression of pathogen-like Opa adhesins in commensal *Neisseria*: genetic and functional analysis," *Cellular Microbiology 3*:33-44, Blackwell Science Ltd. (Jan. 2001).

Troncoso, G., et al., "Analysis of the expression of the putatively virulence-associated neisseria protein RmpM (class 4) in commensal *Neisseria* and *Moraxella catarrhalis* strains," *FEMS Microbiol Lett 199*:171-176, Elsevier Science B.V. (May 2001).

Van der Ley, P. and Poolman, J.T., "Construction of a Multivalent Meningococcal Vaccine Strain Based on the Class 1 Outer Membrane Protein," *Infection and Immunity 60*:3156-3161, American Society for Microbiology (1992).

Van der Ley, P., et al., "Use of Transformation to Construct Antigenic Hybrids of the Class 1 Outer Membrane Protein in *Neisseria meningitidis,*" *Infection and Immunity 61*:4217-4224, American Society for Microbiology (1993).

Office Action for U.S. Appl. No. 09/942,583, Robinson, A., et al., filed Aug. 31, 2001, mailed on Jun. 7, 2005.

* cited by examiner

Challenge dose $10^8$ CFU

Challenge dose 2X10⁷ CFU

Challenge dose 6X10⁸ CFU

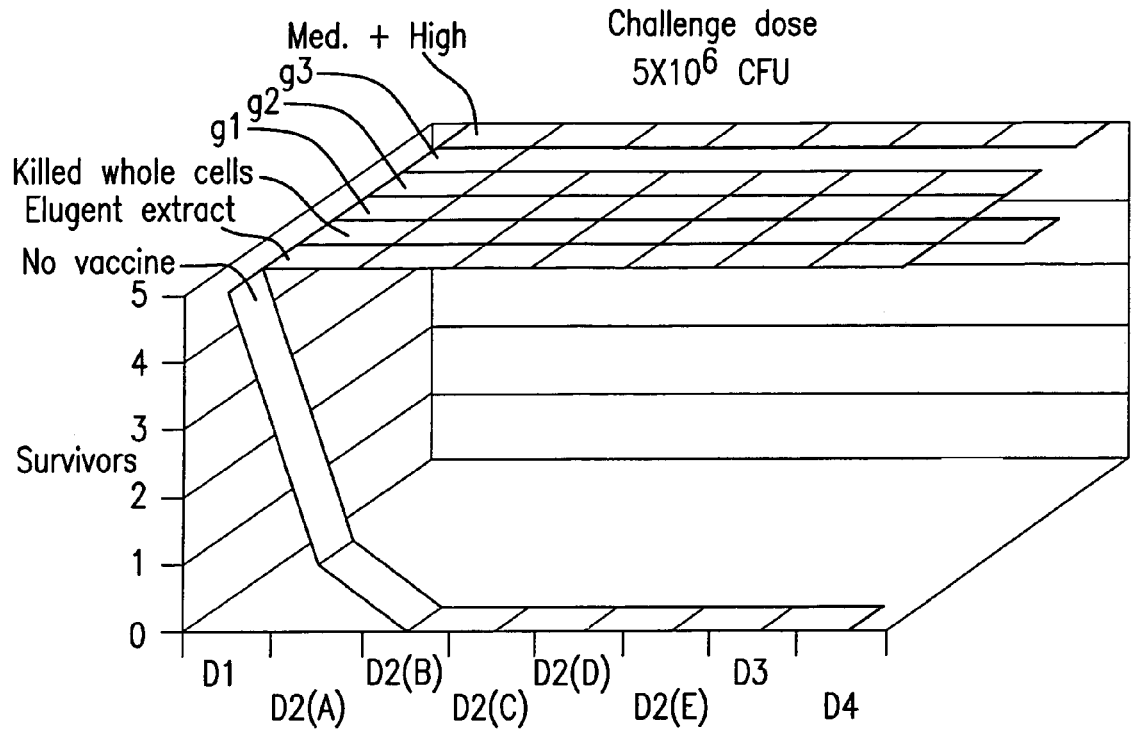
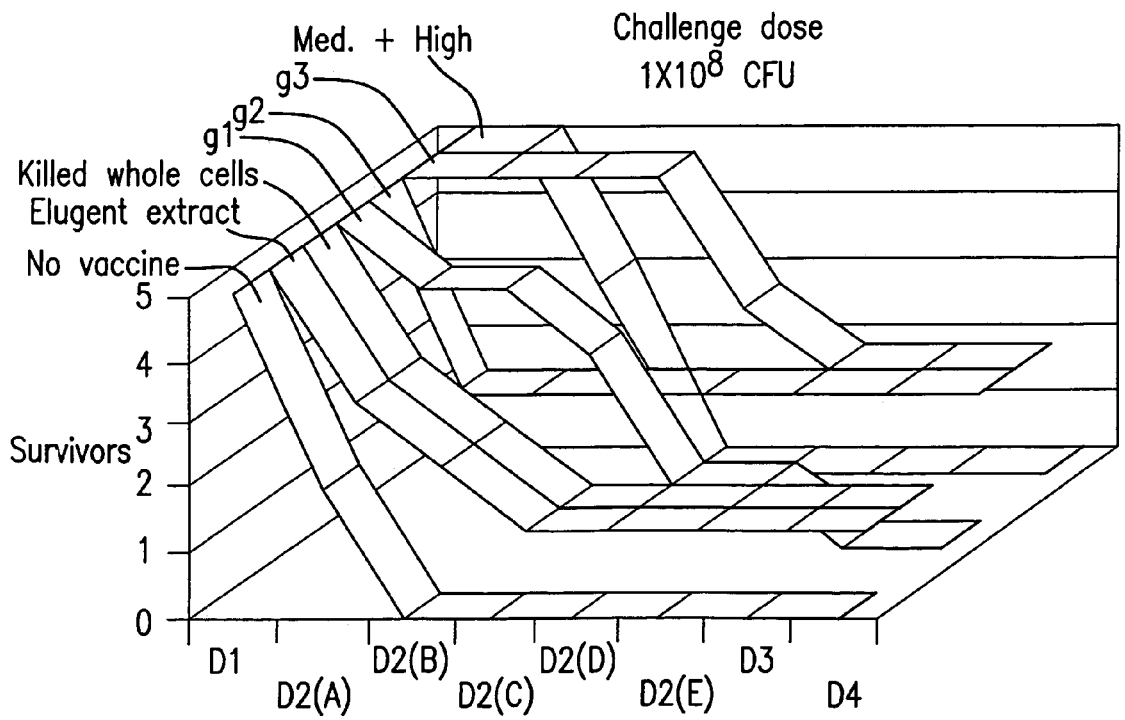

NEISSERIAL VACCINE COMPOSITIONS AND METHODS

The present invention relates to vaccines and methods for preparing vaccines that stimulate an immune response. In particular, the present invention relates to vaccines that provide broad spectrum protective immunity to microbial infection.

Infection by pathogenic organisms is one of the major causes of chronic and acute disease. In particular, infection resulting from microbial sources—such as bacteria, viruses and protozoans—continue to claim millions of lives worldwide. With microbial species increasingly becoming resistant to conventional antibiotics, it would be desirable to provide alternative and preferably prophylactic means of protecting against and fighting microbial infection.

Meningococcal meningitis is of particular importance as a worldwide health problem and in many countries the incidence of infection is increasing. Neisseria meningitidis (the meningococcus) is the organism that causes the disease and is also responsible for meningococcal septicaemia, which is associated with rapid onset and high mortality, with around 22% of cases proving fatal.

At present, vaccines directed at providing protective immunity against meningococcal disease provide only limited protection because of the many different strains of N. meningitidis. Vaccines based upon the serogroup antigens, the capsular polysaccharides, offer only short lived protection against infection and do not protect against many strains commonly found in North America and Europe. A further drawback of these vaccines is that they provide low levels of protection for children under the age of 2 years, one of the most vulnerable groups that are commonly susceptible to infection. Newer conjugate vaccines now in use in the UK will address some of these problems but will only be effective against the C serogroup of the mieningococcus Gold et al. (Journal of Infectious Diseases, volume 137, no. 2, Feb. 1978, pages 112–121) have reported that carriage of N. lactamica may assist in the development of natural immunity to N. meningitidis by induction of cross-reactive antibodies. This conclusion was based on the observation of cross-reacting antibodies having complement-dependent bactericidal activity produced in response to N. lactamica infection. However, Cann and Rogers (J. Med. Microbiol., volume 30, 1989, pages 23–30) detected antibodies to common antigens of pathogenic and commensal neisseria species, but observed also that antibody to the same antigens was present in both bactericidal and non-bactericidal sera. Thus, it was not possible to identify any cross-reactive bactericidal antibodies.

Live attenuated vaccines for meningococcal disease have been suggested by Tang et al. (Vaccine 17, 1999, pages 114–117) in which a live, attenuated strain of N. meningitidis could be delivered mucosally. Tang also commented on the use of commensal bacteria to protect against infection by pathogenic bacteria, concluding that the cross-reactive epitopes that induce protection against meningococcal infection have not been defined, and therefore that use of genetically modified strains of N. meningitidis would be preferred.

It is desirable to provide a further vaccine that gives protective immunity to infection from N. meningitidis. It further is desirable to provide a vaccine that confers protective immunity to infants as well as adults and whose protection is long term. It may also be of advantage to provide a vaccine that protects against sub-clinical infection, i.e. where symptoms of meningococcal infection are not immediately apparent and the infected individual may act as a carrier of the pathogen. It would further be of advantage to protect against all or a wide range of strains of N. meningitidis.

WO-A-96/29412 describes the isolation of a N. meningitidis 22 kDa surface antigen that is immunologically accessible. The 22 kDa antigen. is shown to be conserved in other neisserial species including the commensal N. lactamica.

Aoun et al (Annals de l'Institut Pasteur Microbiol. Vol. 139, pp203–212(1988)) relates to the identification of antibodies in human patients to a 70 kDa meningococcal surface antigen and its value as a vaccine component. Convalescent sera from human carriers was shown to also bind to the 70 kDa protein of N. gonorrheae. However, non-pathogenic Neisseria species although possessing the 70 kDa antigen elicited less frequently an antibody response in children, Gomez et al (Vaccine, Vol. 14, pp 1340–1346 (1996)) describes the purification of a 37 kDa iron-repressible protein (Fbp) from N. menigitidis. Mouse antibodies raised against Fbp from pathogenic Neisseria are shown to bind to Fbps from the commensals N. lactamica and N. sicca, It is an object of the present invention to provide compositions containing immunostimulating components, and vaccines based thereon, that meet or at least ameliorate the disadvantages in the art.

The present invention is based on the use of a commensal Neisseria in a vaccine against disease. Accordingly, a commensal species of Neisseria such as N. lactamica may be used as a live vaccine or a killed whole cell vaccine, or in a vaccine containing fractions of N. lactamica. It has surprisingly been demonstrated that mice immunised according to the present invention with N. lactamica killed whole cells and outer membrane preparations are protected from lethal intraperitoneal meningococcal challenge, and that vaccines composed of a detergent extract of N. lactamica cells or fractions of this, separated by preparative electrophoresis, also protect mice from lethal meningococcal challenge. These results have been obtained using mice and the mouse model used is regarded as predictive of corresponding immunogenic and vaccinating effects in humans.

Accordingly, a first aspect of the present invention provides an immunogenic composition, comprising a commensal Neisseria or an immunogenic component, extract or derivative thereof and a pharmaceutically acceptable carrier.

The composition of the invention is particularly suited to vaccination against infection of an animal. The term "infection" as used herein is intended to include the proliferation of a pathogenic organism within and/or on the tissues of a host organism. Such pathogenic organisms typically include bacteria, viruses, fungi and protozoans, although growth of any microbe within and/or on the tissues of an organism are considered to fall within the term "infection".

Commensal micro-organisms are those that can colonize a host organism without signs of disease. A number of different commensal Neisseria are suitable for use in the invention, and these commensal Neisseria may be selected from the group consisting of N. lactamica, N. cinerea, N. elongata, N. flavescens, N. polysaccharea, N. sicca and N. subflava. Different species of these commensal organisms are known to colonise the buccal or nasal areas or other mucosal surfaces and hence each species may be administered according to the known area of the body it normally colonises. Hence also, use of a composition of the invention may result in stimulation of production of protective antibodies de novo or if the individual has already been colonised to a certain extent may result in an enhancement of naturally-existing antibodies.

The "extract" or "component" is an extract or component that is immunogenic such that antibodies raised aginast the extract or component of a commensal *Neisseria* cross react with a pathogenic *Neisseria*, in particular *N. meningitidis*.

The term "derivative" is used to describe types and strains of commensal *Neisseria* that are modified or attenuated in some way so as to differ from the wild type species; for example, a vaccine composition comprising a recombinant commensal *Neisseria* that exhibits resistance to certain types of antibiotic compounds, which might advantageously be utilised in combination with such antibiotics in the treatment of infection.

It is an advantage of the invention that vaccination against neisserial diseases may thus be achieved using a non-pathogenic species of *Neisseria*, rendering the vaccination a safer procedure. Furthermore, the protection conferred surprisingly may not be restricted to a specific serotype, subtype or serogroup of the meningococcus but is of general protective efficacy.

A further advantage of the invention is that the commensal *Neisseria* that are the subject of the invention can not revert to virulent types. It is known in the vaccination field to use live, attenuated pathogens and this use carries the risk that the attenuated organism may revert to virulence. This risk is avoided by the present invention. Furthermore, *N. meningitidis* possesses many virulence factors the precise roles of which in pathogenesis are unknown and may possess hitherto unrecognised virulence factors. Therefore, an additional advantage of the invention is that a composition of the invention can be used with confidence in its level of safety.

The method of the invention is of application to vaccination against various infections, preferably but not only neisserial infections. In a specific embodiment of the invention, protection against meningococcal disease has been demonstrated. The invention is also of application to vaccination generally against neisserial infection, including gonorrhoeal infection, and also to infection from other pathogenic microbial organisms. The invention further provides for vaccination that is aimed at either stimulating or desensitizing the immune system.

The composition can specifically comprise killed commensal *Neisseria*, which may for example be obtained by heat or by suspending commensal *Neisseria* in a mixture of bactericidal agents such as thiomersal and formaldehyde.

The composition may also comprise live commensal *Neisseria*. As mentioned, it is optional but not usually required to use attenuated commensal *Neisseria* as these organisms are avirulent.

In an embodiment of the invention, an immunogenic component or extract of a commensal *Neisseria* is selected from an outer membrane vesicle preparation, an outer membrane preparation, lipooligosaccharide and a protein fraction.

The outer membrane preparation and protein fraction of *N.lactamica*, for example, can be obtained from *N.lactamica* cultured in the presence or absence of iron. The protein fraction of *N.lactamica* is conveniently obtained by suspending *N.lactamica* cells or membranes in the presence of detergent and incubating the suspension so as to extract proteins from the *N.lactamica*.

Alternatively, a number of other techniques are known for extraction of outer membrane components—such as protein fractions, lipooligosaccharides and lipopolysaccharides— from cell preparations and are suitable to obtain the commensal *Neisseria* immunogenic components or extracts of the invention. Examples of conventional techniques for this purpose include the use of variation in salt concentration, chaotropic agents, variation in pH (high or low), enzymic digestion and mechanical disruption.

A number of different fractions are suitable for use in vaccinating against meningococcal disease. Particularly suitable fractions are those of molecular weight less than 50 kDa, of molecular weight more than 40 kDa and less than 70 kDa, and of molecular weight more than 60 kDa.

In more specific embodiments of the invention there is provided a composition for eliciting an immune response and suitable for use in vaccinating an individual against neisserial infection, more specifically meningococcal disease, comprising an antigenic component or antigenic components having the properties:

(a) molecular weight 50 kDa or lower;
(b) obtainable from *N. lactamica*; and
(c) antibodies to the component(s) obtained from *N. lactamica* cross-react with *N. meningitidis*.

In use of a composition containing such a component, extracted using detergent, all mice treated with this component survived a challenged dose of $2 \times 10^7$ CFU *N. meningitidis* and three out of five mice survived a higher challenge dose of $6 \times 10^8$ CFU.

Another specific embodiment of the invention lies in a composition for eliciting an immune response and suitable for use in vaccinating an individual against neisserial infection, more specifically meningococcal disease, comprising an antigenic component or antigenic components having the properties:

(a) molecular weight at least 40 kDa and up to 70 kDa;
(b) obtainable from *N. lactamica*; and
(c) antibodies to the component(s) obtained from *N. lactamica* cross-react with *N. meningitidis*.

In use of such a component of the invention, obtained using a detergent extract of *N. lactamica*, four out of five mice treated with the component survived a challenge dose of $2 \times 10^7$ CFU *N. meningitidis* and mice receiving a higher challenge dose of $6 \times 10^8$ CFU survived longer than a control group.

A still further embodiment of the invention lies in a composition for eliciting an immune response and suitable for use in vaccinating an individual against neisserial infection, more specifically meningococcal disease, comprising an antigenic component or antigenic components having the properties:

(a) molecular weight at least 60 kDa;
(b) obtainable from *N. lactamica*; and
(c) antibodies to the component(s) obtained from *N. lactamica* cross-react with *N. meningitidis*.

In use of such a component, obtained using a detergent extract, one out of five mice survived a challenge dose of $2 \times 10^7$ CFU *N. meningitidis* and, whilst all mice succumbed to a higher challenged dose of $6 \times 10^8$ CFU, their survival time was longer than a control group which did not receive the component.

In an example of the invention in use, described in more detail below, proteins in the size ranges of 25–35 kDa and 35–43 kDa, extracted from a commensal *Neisseria*, conferred a significant level of immune protection when administered to mice as a vaccine composition.

By way of example of a method of extracting an antigenic component of the invention, an extraction method comprises:

(i) suspending *N.lactamica*, cells in an aqueous solution of detergent;
(ii) incubating the suspension so as to extract the antigenic component from the *N.lactamica*;

(iii) centrifuging the suspension to separate the suspension into a supernatant and a pellet; and
(iv) fractionating the antigenic component from the supernatant.

This specific method can be modified according to the extraction protocol selected by the user, for example by using high salt concentration in the initial step (i). In further embodiments of the invention the antigenic component is obtained using recombinant technology by expression of a *N. lactamica* sequence in a suitable host such as *E. coli.*

In a second aspect of the invention there is provided a composition for vaccination against neisserial infection comprising a commensal *Neisseria* or an immunogenic component, extract or derivative thereof and a pharmaceutically acceptable carrier, wherein the commensal *Neisseria* comprises and expresses a gene from a pathogenic *Neisseria.*

This aspect of the invention offers the benefit of use of a commensal organism to deliver and/or present to the recipient an antigen from a pathogenic *Neisseria*. The gene optionally encodes a surface antigen or a protein that is secreted, and may code for an antigen from, for example, *N. meningitidis* or *N. gonorrhoeae*. The commensal *Neisseria* can be live or killed.

In an embodiment of the second aspect of the invention there is provided a composition for vaccination against meningococcal disease comprising a commensal *Neisseria* and a pharmaceutically acceptable carrier, wherein the commensal *Neisseria* comprises and expresses a *N. meningitidis* gene.

The *N. meningitidis* gene may encode for example a transferrin binding protein, a superoxide dismutase (SOD) for example a Cu,Zn SOD, neisserial surface protein A ("NspA"), a porin or another outer membrane protein. Gene sequences for the majority of these antigens are known in the literature. Kroll et al. in Microbiology 141 (Pt 9), 2271–2279 (1995) describe the sequence of Cu,Zn-SOD. Martin et al. in J Exp Med, Apr. 7, 1997, 185(7), pp 1173–1183 describe the sequence of NspA from *N. meningitidis.*

The invention also provides a pharmaceutical composition comprising a composition according to the first or second aspect of the invention plus a pharmaceutically acceptable carrier.

In a third aspect, the invention provides a method of vaccination against neisserial infection, comprising administering an effective amount of a composition according to the first and second aspects of the invention.

In use of an embodiment of the invention described in an example below, there is provided a method of vaccination against meningococcal disease, comprising administering an effective amount of a composition according to the first and second aspects of the invention.

In a fourth aspect of the invention there is provided a strain of a commensal *Neisseria*, such as *N. lactamica*, genetically modified so as to express a gene from a pathogenic *Neisseria*. The *N.meningitidis* gene may for example code for a protein selected from a transferrin binding protein, a SOD for example a Cu,Zn-SOD, NspA, a porin or another outer membrane protein.

The invention further provides, in a fifth aspect a method of extracting a protein for incorporation in a composition suitable for vaccinating against meningococcal disease, comprising:

(i) suspending commensal *Neisseria*, for example *N.lactamica*, cells in the presence of detergent; and (ii) incubating the suspension so as to extract a protein fraction from the cells.

The protein fraction can suitably be of molecular weight 50 kDa or lower, at least 40 kDa and up to 90 kDa or at least 80 kDa.

The composition may be combined with a pharmaceutically acceptable carrier—for example the adjuvant alum although any carrier suitable for oral, intravenous, subcutaneous, intraperitoneal intramuscular, intradermal or any other route of administration is suitable—to produce a pharmaceutical composition for treatment of meningococcal disease. Commensal *Neisseria* that are buccal colonizers can be administered in a mouthwash and nasal colonizers in a nasal spray.

Transferrin binding proteins are known to be located on the outer membranes of a number of Gram negative bacteria such as *N. meningitidis*. Formulations of the composition of the present invention with conventional carriers or adjuvants and optionally further supplemented by one or more antigens from *Neisseria* species, optionally recombinantly produced, for example, Cu—Zn SOD, the 22 kD NspA, porins, gonorrhoeal antigens or transferrin binding proteins provide a composition for treatment of infection by these bacteria.

In the present invention, the term "transferrin binding protein" or "Tbp" refers to a protein which either alone binds to transferrin or can be part of a complex of proteins that binds transferrin. The term also embraces fragments, variants and derivatives of such a protein provided that antibodies raised against the fragment, variant or derivative bind the protein. Thus, TbpA and TbpB either dissociated or associated into a complex are considered to be Tbp. Moreover, mutants, fusion proteins or fragments of either TbpA or B or other derivatives of the TbpA+B complex with a common antigenic identity are also considered to be represented by the term Tbp in the present invention.

A live vaccine according to the present invention may be administered parenterally or to the mucosa for example via intranasal or oral inoculation. A killed bacteria or subunit vaccine may also be given by this route, or formulated for oral delivery. A subunit vaccine is conveniently administered via the parenteral route. Different commensal *Neisseria* and different strains of *N. lactamica* from those tested in specific embodiments of the invention exist, and the invention is of application also to those other strains.

A sixth aspect of the invention provides a composition comprising an antibody, wherein the antibody binds to a commensal *Neisseria* of the first or second aspects of the invention or an immunogenic component or extract thereof. In use, the antibody can be formulated into a pharmaceutical composition for treatment of neisserial infection, such as meningococcal disease or infection caused by other *Neisseria.*

An antibody according to this aspect of the invention can be obtained following standard techniques, for example by inoculating an animal with the commensal *Neisseria* or an immunogenic component or extract thereof and thereafter isolating antibodies that bind to the commensal *Neisseria* or the immunogenic component or extract thereof.

A further aspect of the invention provides for a composition comprising a commensal *Neisseria*, or an immunogenic component, extract or derivative thereof, wherein said *Neisseria* comprises a heterologous gene product.

Heterologous gene products of the invention typically include peptides, proteins and antisense sequences that are coded for by a gene sequence that is not native to the commensal *Neisseria*. Typical heterologous gene products of the invention include, for example, bacterial proteins, viral proteins or surface peptides, antigens and antibodies and fragments thereof. The heterologous gene product of the invention may also be any antigen found in a pathogenic organism.

In an embodiment of the invention, the composition comprises a commensal *Neisseria* into which has been transformed an expression vector containing a gene sequence encoding a heterologous gene product. Specific proteins suitable for use in the invention typically include:

Viral proteins—such as hepatitis B virus surface antigen; rabies virus glycoprotein G; herpes simplex virus glycoprotein D; Epstein-Barr virus glycoprotein; influenza virus glycoprotein; vesicular stomatitis virus nucleoprotein; human respiratory syncytial virus glycoprotein G; human immunodeficiency virus (HIV) envelope; rotavirus subunits; measles virus subunits; and vaccinia virus subunits.

Bacterial proteins—such as *Bordetella pertussis* fimbrial subunits; *Bordetella pertussis* surface proteins; *Bacillus anthracis* subunits; *Escherichia coli* subunits; and *Yersinia pestis* subunits. Protozoan proteins—such as *Plasmodium falciparum* proteins; trypanosome proteins; and *Cryptosporidium* proteins.

In a further embodiment the composition of the invention suitably provides for a commensal *Neisseria* that expresses a heterologous gene product which is immunostimulatory for treatment of non-infectious disease, for example allergy and cancer. In an example of the invention in use a commensal *Neisseria* that expresses peanut antigens is used to desensitize a patient with acute peanut allergy.

In a further example of the invention in use, described in more detail below, the expression vector pJSK422 is used to express green fluorescent protein, under the control of the groES/EL promoter, in the commensal *N. cinerea*.

The invention further provides for a commensal *Neisseria* that is transformed with an expression vector that comprises a signal sequence that directs the heterologous gene product to the outer membrane of the neisserial cell. Other signal sequences are also suitable for use in the invention, such as secretion signals or cellular subcompartment localisation signals e.g. periplasmic localisation signals.

Further aspects of the invention provide methods for preparing compositions. Such methods are suitable for preparing vaccine compositions that elicit protective immunity to microbial infection when administered to an animal.

An example of the invention in use, described in more detail below, provides for a method of preparing a composition comprising the steps of:

a) inserting a gene coding for a heterologous gene product into an expression vector;

b) transforming said expression vector into a commensal *Neisseria* so that said heterologous gene product is expressed in said *Neisseria*; and c) combining the *Neisseria* of (b) with a pharmaceutically acceptable carrier.

A further example of the invention, provides for a method of preparing a composition comprising the steps of:

a) inserting a gene coding for a heterologous gene product into an expression vector;

b) transforming said expression vector into a commensal *Neisseria* so that said heterologous gene product is expressed in said *Neisseria*;

c) obtaining an immunogenic component or extract from the *Neisseria* of (b); and d) combining the immunogenic component or extract of (c) with a pharmaceutically acceptable carrier.

In yet a further example of the invention in use is provided a method of preparing a composition comprising the steps of:

a) obtaining an immunogenic component or extract from a commensal *Neisseria*; and b) combining the immunogenic component or extract of (a) with a heterologous gene product and a pharmaceutically acceptable carrier.

Thus, the invention provides for (a) methods and compositions in which an extract is taken from a commensal *Neisseria* that expresses a heterologous gene product, and (b) methods and compositions where an extract is obtained from a commensal *Neisseria* and the heterologous gene product expressed elsewhere (in another organism) is combined with this latter extract.

Further aspects of the invention provide for use of a commensal *Neisseria* in the manufacture of a medicament for treatment of neisserial infection, and for use of a commensal *Neisseria*, or an immunogenic component, extract or derivative thereof, wherein said *Neisseria* comprises a heterologous gene product, in the manufacture of a medicament for the treatment of infection or for immunostimulation in an animal.

Specific embodiments of the invention are discussed in more detail by means of the Examples described below. The results referred to in the Examples are illustrated by the accompanying drawings, in which:

FIG. 5 shows protection of mice against IP infection with *N. meningitidis* strain K454 when immunised with low molecular weight subfractions—FIG. 5A=challenge by $5 \times 10^6$ CFU, FIG. 5B=challenge by $1 \times 10^8$ CFU.

EXAMPLE 1

Figure 1:
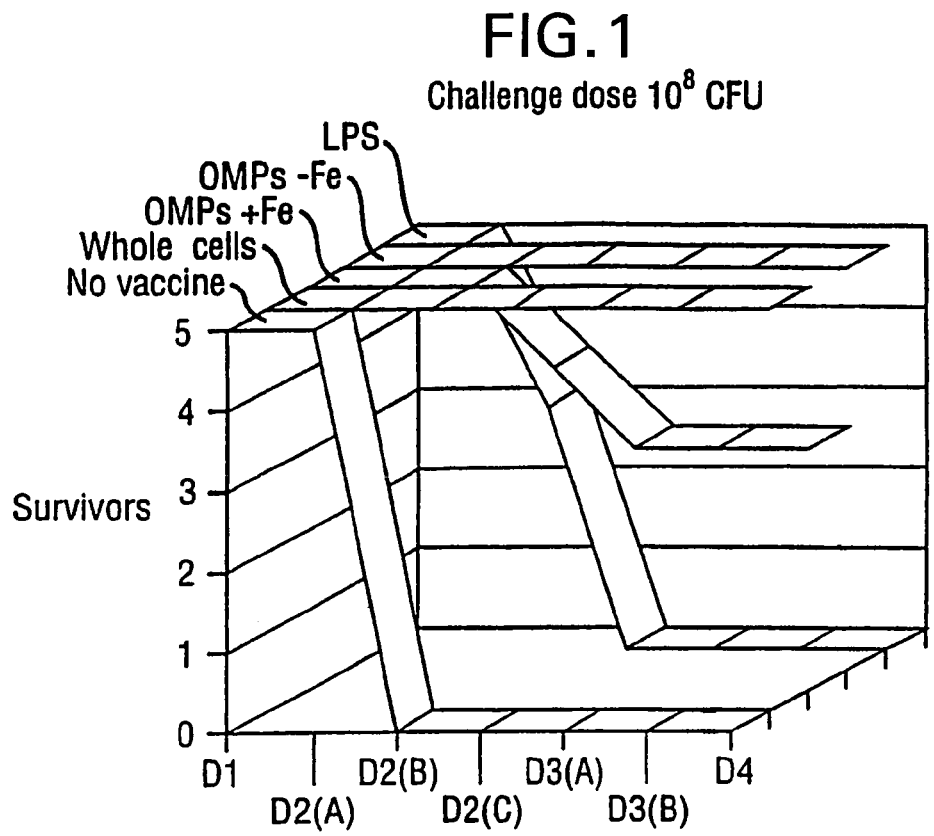
FIG. 1 shows protection of mice against intraperitoneal ("IP") infection with *N.meningitidis* strain K454 by use of *N.lactamica* whole cells and outer membrane fractions.

Preparation of Vaccine Containing Killed Whole Cells

*Neisseria lactamica* strain Y92-1009 was grown in Mueller Hinton broth (MHB) containing 5 µgml$^{-1}$ ethylenediamine-di(o-hydroxyphenylacetic acid) (EDDHA), incubated at 37° C. with shaking (140 rpm) for approximately 6 h.

Bacteria were then harvested by centrifugation and resuspended in phosphate buffered saline (PBS) containing 1% (v/v) formaldehyde and 0.1% (w/v) thiomersal, and left to stand overnight at 2–8° C. Killed cells were then resuspended in PBS to an OD$_{650}$ of 1.0 (equivalent to $2 \times 10^9$ CFUml$^{-1}$) and an aluminium hydroxide adjuvant (Alhydrogel™) [alhydrogel (Registered Trade Mark)] added to 25% (V/V), yielding a product suitable for subcutaneous administration.

This method is suitable also for *N. cinerea, N. elongata, N. flavescens, N. polysaccharea, N. sicca* and *N. subflava*.

EXAMPLE 2

Preparation of Vaccine Containing *N. lactamica* Outer Membrane (OM) Preparations

*N. lactamica* strain Y92-1009 was grown in MHB with and without the addition of 5 μgml$^{-1}$ EDDHA overnight at 37° C. with shaking. Iron limited (with EDDHA) and iron replete cells were then treated separately. Bacteria from 1.5 liters were harvested by centrifugation and resuspended in 20 ml 200 mM Lithium acetate, 5 mM EDTA, pH 6.0 and incubated for 3 h at 37° C. with shaking. Bacteria were then passed 7 times through a 21 gauge needle and pelleted at 8000 g for 10 min.

The supernatant was recovered and membranes pelleted by centrifugation at 100,000 g for 1 h at 4° C. The membranes were then resuspended in 10 mM HEPES, pH 7.4, containing 0.1% (v/v) 10 mM PMSF, yielding OM-containing vaccinating preparations. The protein content of the OM vaccine preparations was determined using the bicinchoninic acid assay (Sigma, UK). OMs were diluted in sterile deionized water to give a protein concentration of 100 μgml$^{-1}$. This was then mixed with an equal volume of Freund's adjuvant, to give a final protein concentration of 50 μgml$^{-1}$, and emulsified thoroughly. Freund's complete adjuvant was used for the primary dose, and Freund's incomplete for subsequent boosts.

EXAMPLE 3

Preparation of Vaccine Containing Lipooligosaccharide (LOS)

Purification of LOS was carried out from *N. lactamica* strain Y92-1009 using the method of Gu, X-X and Tsai, C. M. (1991) Anal Biochem. 196; 311–318. Vaccine was prepared using Freund's adjuvant as above with LOS at a final concentration of 10 μgml$^{-1}$.

EXAMPLE 4

Vaccination and Challenge Schedule

Groups of 5 mice were vaccinated with each preparation as follows:

| | |
|---|---|
| Prime: | Day 0 |
| First boost: | Day 21 |
| Second boost: | Day 28 |

Mice vaccinated with killed cells of Example 1 received 0.5 ml subcutaneously, equivalent to 1×10$^9$ CFU. Mice vaccinated with OM of Example 2 and LOS of Example 3 received 0.2 ml subcutaneously; equivalent to 10 μg of protein and 2 μg of LOS.

On day 35, mice were challenged by intraperitoneal injection with approximately 10$^8$ CFU *N. meningitidis* K454 made up in MHB containing transferrin at a final concentration of 20 mg/ml. The mice were then examined and the number of survivors noted and the results are shown in FIG. 1. After 4 days all 5 mice survived in the groups vaccinated with whole cells and OMPs (without iron) and 3 survived in the group vaccinated with OMPs (with iron). After 5 days all members of the control group and of the group vaccinated with LOS (marked LPS on the figure) had died.

EXAMPLE 5

Preparation of Vaccine Comprising *N. lactamica* Fractions

Brain heart infusion agar plates were inoculated with 50 μl of *N. lactamica* strain Y92-1009 and incubated overnight at 37° C., with 5% $CO_2$. This was used to inoculate a 100 ml MHB starter culture which was incubated with shaking at 37° C. for 6 h. Starter culture (15 ml) was added to each of 6×500 ml volumes of MHB. These were then incubated with shaking overnight at 37° C. and the conditions were made iron-limited by the addition of 5 ugml$^{-1}$ EDDHA. The cells were harvested by centrifugation and the supernatant discarded. The cells were washed with 100 ml PBS and then pelleted by centrifugation. Cell pellets were resuspended in PBS +0.3% (v/v) Elugent™ detergent [Elugent (Registered Trade Mark)] (Calbiochem, 2 ml per g wet weight) and incubated with shaking at 37° C. for 20 min. The cells were then removed by centrifugation and the pellet discarded. EDTA and N-lauroyl sarcosine were then added to the supernatant to 10 mM and 0.5% (w/v) respectively.

The BioRad™ Prep Cell, model 491 electrophoresis unit was then used to separate the proteins contained in the detergent extract. A 4 cm, 7% acrylamide native resolving gel was cast with a 2 cm stacking gel. 12 mg of protein in native sample buffer was electrophoresed using running buffer containing 0.1% (w/v) SDS, 0.02 5M Tris and 0.192M glycine at 40 mA and 400V until the dye front reached the bottom of the gel. 3 ml fractions of the eluted proteins were then collected. Once the fractions were collected they were pooled into groups consisting of proteins of molecular weight approximately less than 40 kDa, between 40 and 67 kDa and more than 67 kDa. The pooled proteins were concentrated by ammonium sulphate precipitation and dialysed against PBS. These were diluted in PBS to a protein concentration of 100 ug/ml and Freund's complete adjuvant was added at a ratio of 1:1 (v/v) or Freund's incomplete adjuvant for booster doses.

EXAMPLE 6

Vaccination and Challenge Schedule

Groups of 5 mice were vaccinated with each preparation as follows:

| | |
|---|---|
| Prime: | Day 0 |
| First boost: | Day 21 |
| Second boost: | Day 28 |

Mice were vaccinated with no vaccine (i.e. control group), Elugent™ [alhydrogel (Registered Trade Mark)] extract or high, medium or low molecular weight fraction. The mice receiving the protein fraction groups received 0.2 ml subcutaneously; equivalent to 10 μg of protein.

Figure 2A:
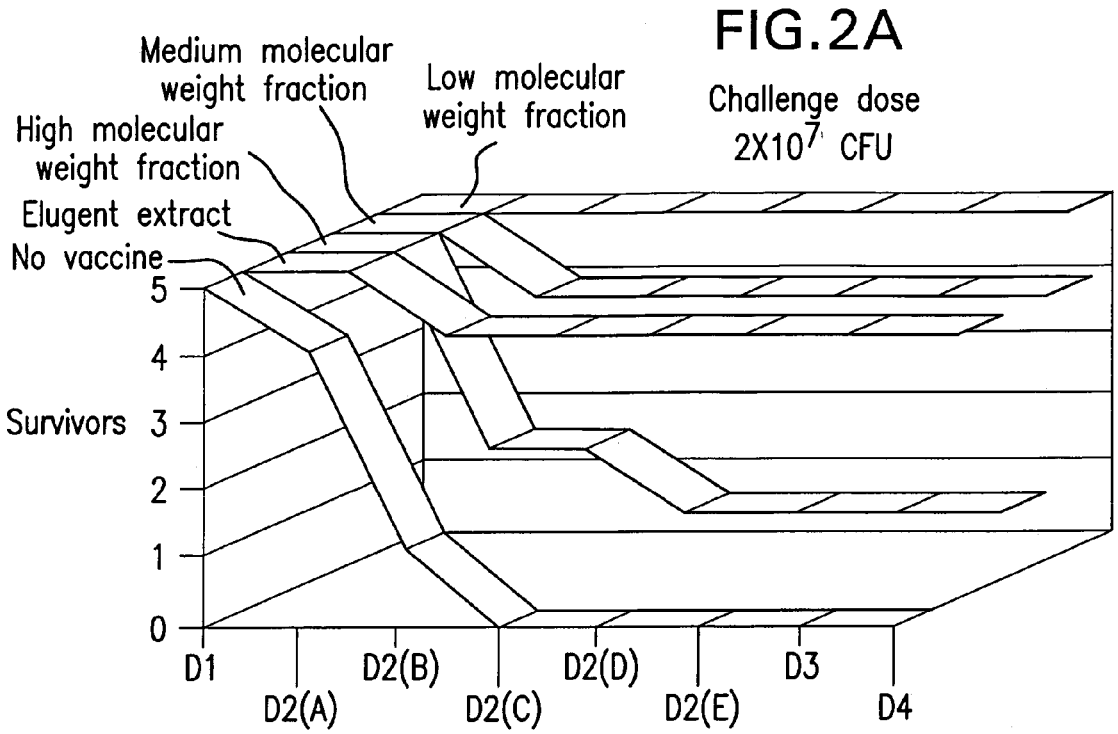
FIGS. 2A and 2B show protection of mice against IP infection with *N. meningitidis* strain K454 by use of detergent and high, medium and low molecular weight extracts of *N. lactamica* cells—FIG. 2A=challenge by $2 \times 10^7$ CFU, FIG. 2B=challenge by $6 \times 10^8$ CFU.
Figure 2B:
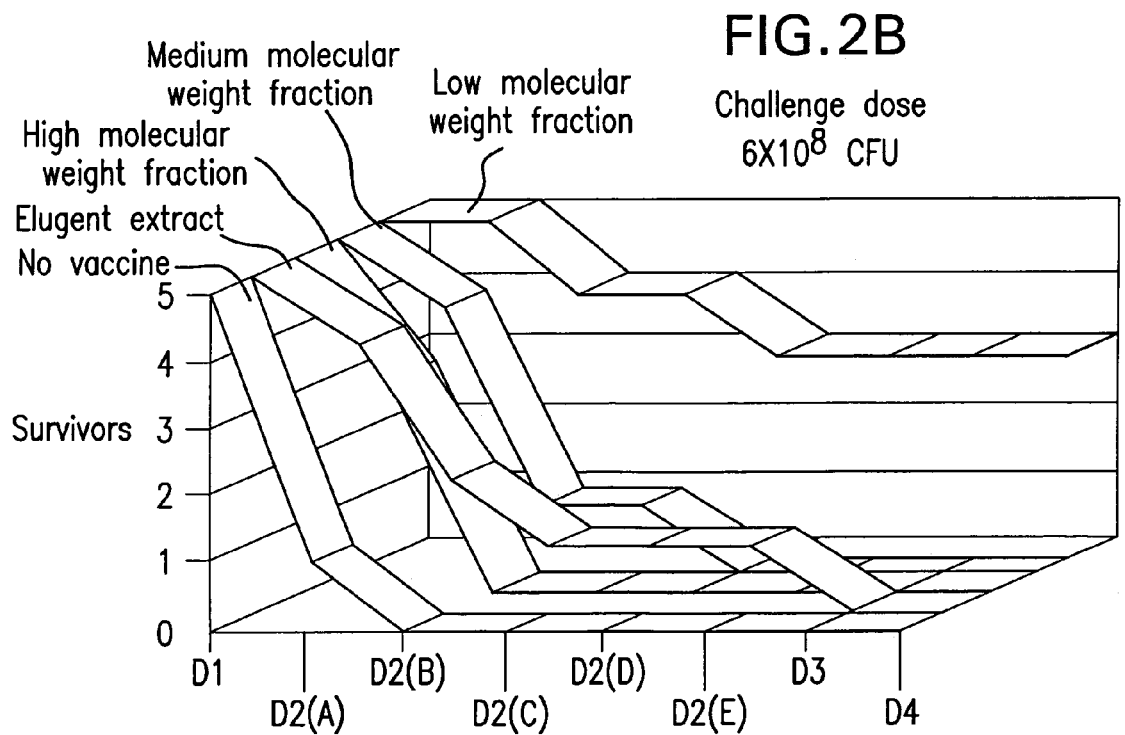
Figure 2C:
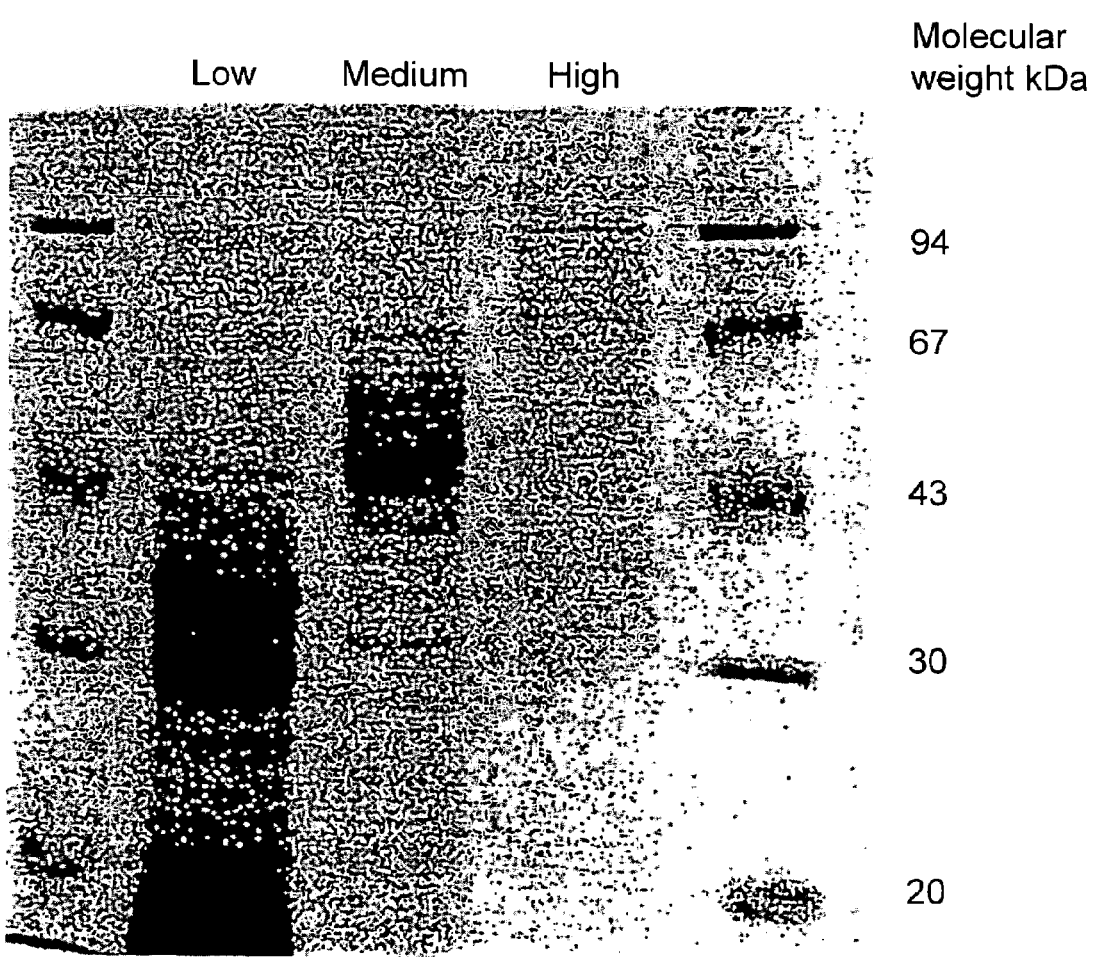
FIG. 2C shows the components of the high, medium and low molecular weight fractions of FIGS. 2A and 2B.

On day 35 mice were challenged by intraperitoneal injection with either approximately 2×10$^7$ or 6×10$^8$ CFU *N. meningitidis* K454 made up in MHB containing transferrin at a final concentration of 20 mg/ml. The mice were then examined over four days and the number of survivors noted, and the results are shown in FIG. 2A (2×10$^7$ challenge) and FIG. 2B ($6 \times 10^8$ challenge). The components of the high, medium and low molecular weight fractions are shown in FIG. 2C. after being run on an SDS-PAGE gel.

EXAMPLE 7

Figure 3:
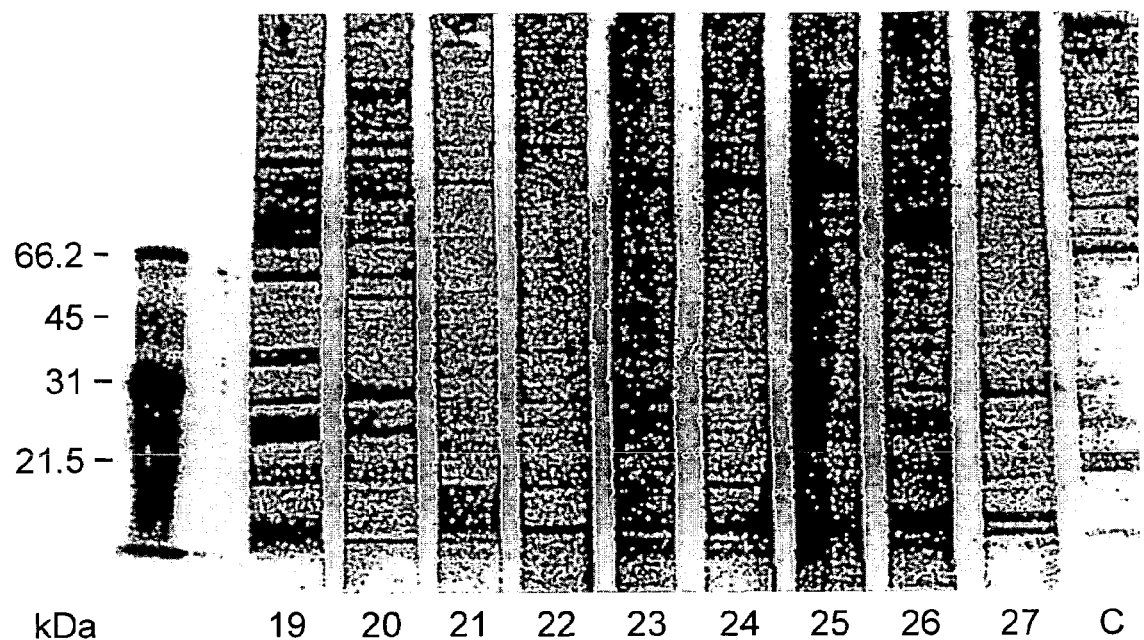
FIG. 3 shows an immunoblot illustrating cross-reaction of antibodies in sera from meningococcal disease patients with proteins from *N. lactamica*

Samples of human sera following meningococcal disease were investigated and these showed that antibodies were produced which react with a range of *N. lactamica* proteins. The results of the immunoblot are shown in FIG. 3.

EXAMPLE 8

Figure 4:
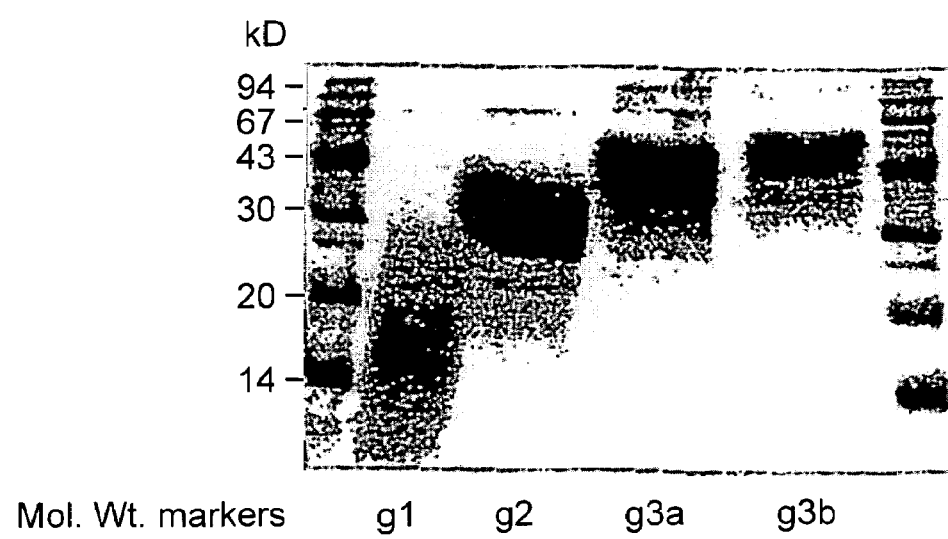
FIG. 4 shows a photograph of a gel on which subfractions of low molecular weight outer membrane protein extract have been run.

Due to the level of protection offered by the low molecular weight pool in Example 6 (see FIGS. 2A and 2B), further separation of these proteins was carried out, according to the method of Example 5, to further characterise components responsible for protection. Proteins were pooled into three groups consisting of <25 kDa (g1), 25–35 kDa (g2) and 35–43 kDa (g3)(shown in FIG. 4). Determination of the levels of lipopolysaccharide (LPS) revealed high levels of LPS in fraction g1 [26 580 endotoxin units per ml (EUml$^{-1}$)], and considerably lower levels in the remaining fractions (9149 EUml$^{-1}$ in g2 and 9348 EUml$^{-1}$ in g3).

As in previous examples, groups of five mice were immunised, using a three dose schedule with one of the three groups of proteins described above, proteins >43 kDa and detergent extract of killed whole *N. lactamica* cells and killed whole *N. lactamica*. Animals were challenged with *N. meningitidis* serogroup B, strain K454, at a dose of $5 \times 10^6$ or $1 \times 10^8$ CFU, together with unimmunised controls. The number of survivors on each day post challenge is shown in FIG. 5.

All mice, apart from the control group and one mouse in group g3, survived the lower challenge dose; however, at the higher challenge dose the g2 and g3 protein groups (25–35 kDa and 35–43 kDa respectively) offered best protection.

EXAMPLE 9

Commensal *Neisseria* as a Vehicle for Recombinant Protein Expression

The gene encoding the measles virus nucleocapsid protein was cloned into the pMGC18.1 shuttle vector (Webb et al., 1998, poster at the 11$^{th}$ International Pathogenic *Neisseria* Conference, Nice) and transformed into *E.coli* DH5alpha. Expression of the measles virus nucleocapsid protein was confirmed by western blotting probed with specific antiserum. This construct was then used to transform *N. lactamica* by conjugation. Expression of the measles virus nucleocapsid protein was placed under the control of the neisserial frpC promoter and expression at high levels was seen when the bacteria were grown under iron-limited growth conditions.

EXAMPLE 10

Expression of GFP in the Commensal *N. cinerea*

The green fluorescent protein (GFP) gene of *Aequorea victoria* was inserted into the pJSK422 plasmid using standard cloning techniques. The GFP was under the control of the groES/EL promoter. As a negative control the GFP gene was also inserted into the pJSK411 plasmid which lacks the groES/EL promoter of the pJSK422 plasmid.

Figure 6:
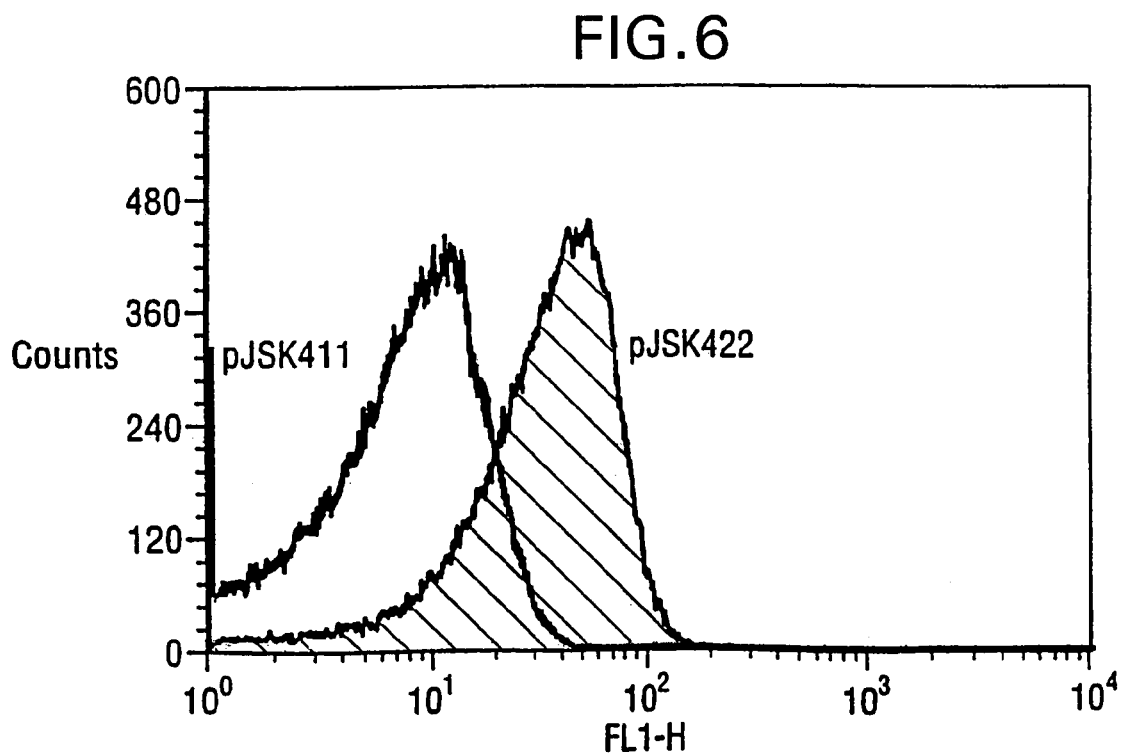
FIG. 6 shows a histogram comparing the fluorescence of *N. cinerea* NRL 32165 containing pJSK411 (promoterless GFP) to pJSK422 (pJSK411 with groEL/ES promoter).

*N. cinerea* was transformed via conjugation (see Example 9) either with the pJSK422 or pJSK411 (negative control) GFP containing plasmids. The transformed cells were cultured under appropriate conditions. Fluorescence of the pJSK422 transformed cultures of *N. cinerea* were compared to that of the pJSK411 transformed cultures. The results of the comparison are shown in FIG. 6. The histogram shows intensity of GFP fluorescence on the X axis and the number of cells fluorescing on the Y axis. It is clear that the level of fluorescence is higher in the *N. cinerea* transformed with pJSK422 than those transformed with pJSK411, indicated by the peak shift to the right. This, demonstrates heterologous expression of the GFP gene in the commensal *N. cinerea*.

The invention thus provides immunogenic compositions and vaccines for use in protecting against disease.

The invention claimed is:

1. A composition comprising an outer membrane preparation or an outer membrane vesicle preparation of a commensal *Neisseria* that expresses a gene product heterologous to said commensal *Neisseria*.

2. The composition of claim 1, wherein said cormnensal *Neisseria* is selected from the group consisting of *N. lactamica*, *N. cinerea*, *N. elongata*, *N. flavescens*, *N. polysaccharea*, *N. sicca*, and *N. subflava*.

3. The composition of claim 1, wherein said commensal *Neisseria* is *N. lactamica*.

4. The composition of claim 1, wherein said heterologous gene product is of a pathogenic *Neisseria*.

5. The composition of claim 1, wherein said heterologous gene product is selected from the group consisting of a transferrin binding protein, a porin, Neisserial surface protein A (NspA), an outer membrane protein, and a Cu, Zn-superoxide dismutase.

6. The composition of claim 1, wherein said preparation is extracted from said commensal *Neisseria*.

7. A composition comprising an outer membrane preparation or an outer membrane vesicle preparation of a commensal *Neisseria* which comprises and expresses a gene of a pathogenic *Neisseria* and a pharmaceutically acceptable carrier.

8. The composition of claim 7, wherein said commensal *Neisseria* is selected from the group consisting of *N. lactamica*, *N. cinerea*, *N. elongata*, *N. flavescens*, *N. polysaccharea*, *N. sicca*, and *N. subflava*.

9. The composition of claim 7, wherein said commensal *Neisseria* is *N. lactamica*.

10. The composition of claim 7, wherein said gene is a *N. meningitidis* gene which codes for a protein selected from the group consisting of a transferrin binding protein, a porin, Neisserial surface protein A (NspA), an outer membrane protein, and a Cu, Zn-superoxide dismutase.

11. The composition of claim 7, wherein said preparation is extracted from said commensal *Neisseria*.

* * * * *